United States Patent [19]

Peterson

[11] Patent Number: 5,160,261
[45] Date of Patent: Nov. 3, 1992

[54] ORTHODONTIC BRACKET AND METHOD
[75] Inventor: Jeffrey A. Peterson, Aurora, Colo.
[73] Assignee: RMO, Inc., Denver, Colo.
[21] Appl. No.: 702,943
[22] Filed: May 20, 1991
[51] Int. Cl.[5] .............................................. A61C 3/00
[52] U.S. Cl. .......................................... 433/8; 433/10
[58] Field of Search ................... 433/8, 9, 10, 13, 15, 433/18, 16

[56] References Cited

U.S. PATENT DOCUMENTS

| | | | |
|---|---|---|---|
| 1,890,487 | 12/1932 | Angle . | |
| 3,854,207 | 12/1974 | Wildman | 32/14 |
| 4,103,423 | 8/1978 | Kessel | 32/14 |
| 4,260,375 | 4/1981 | Wallshein | 433/11 |
| 4,669,981 | 6/1987 | Kurz | 433/9 |
| 4,712,999 | 12/1987 | Rosenberg | 433/8 |
| 4,793,804 | 12/1988 | Schudy | 433/8 |
| 4,799,882 | 1/1989 | Kesling | 433/8 |
| 4,819,316 | 4/1989 | Rossini et al. | 433/8 |
| 5,062,794 | 11/1991 | Miura | 433/10 |

FOREIGN PATENT DOCUMENTS 0379668  8/1990  European Pat. Off. .............. 433/10

Primary Examiner—Cary E. O'Connor
Attorney, Agent, or Firm—Sheridan Ross & McIntosh

[57] ABSTRACT

An edgewise bracket (10) is provided with notches (34, 36, 38 and 40) in wing tips (24, 25, 26 and 27), respectively. The notches (24, 25, 26 and 27) are generally concave and have a mesiodistal width slightly greater or slightly less than the thickness of an archwire retaining device (32) depending on whether the device (32) is a metallic wire or an elastomeric ligature. The archwire retaining device (32) is inserted into the notches (34, 36, 38, and 40) to retain an archwire (30) within a slot (28) which has a depth greater than a thickness of the archwire (30). The device (32) has selectively reduced undesired frictional contact with the archwire (30), and, therefore, frictional interference between the device (32) and the archwire (30), and the archwire (30) and the bracket (10) is reduced or eliminated.

36 Claims, 4 Drawing Sheets

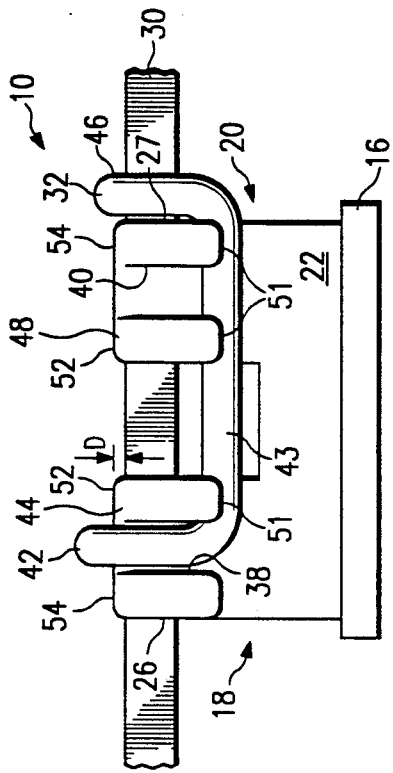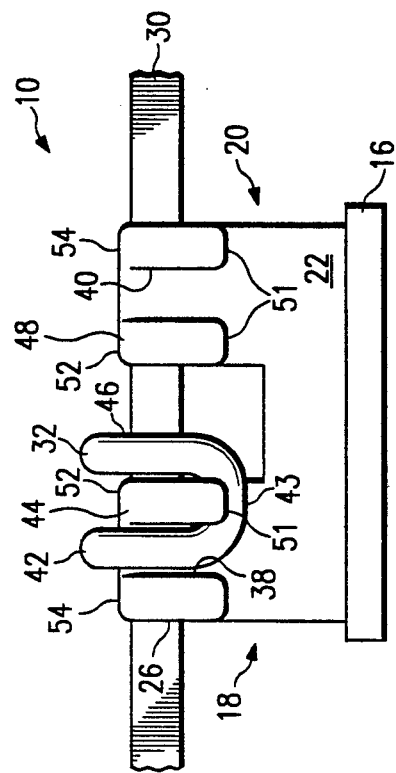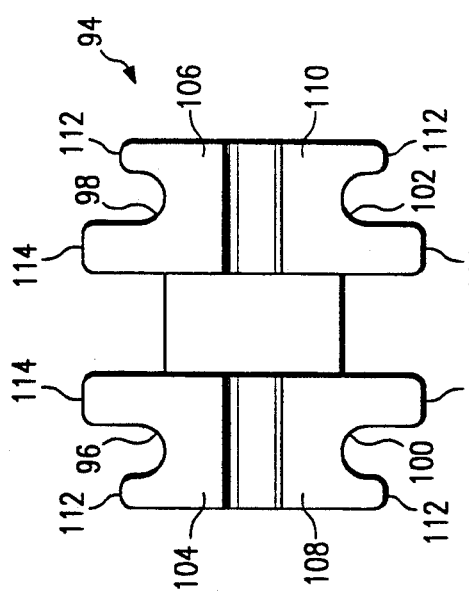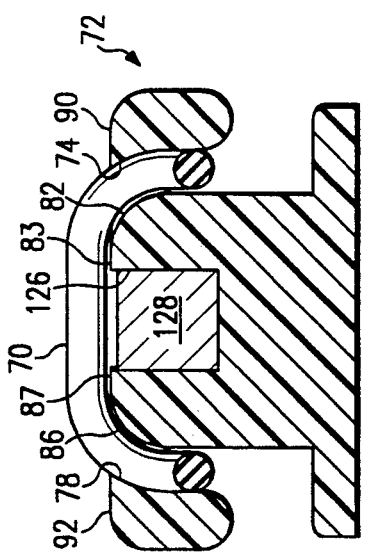

ORTHODONTIC BRACKET AND METHOD

TECHNICAL FIELD OF THE INVENTION

This invention relates in general to orthodontic brackets of the edgewise type, and in particular to a double edgewise bracket having notches on the outside edges of one or both pairs of wing tips for supportive engagement of a ligature.

BACKGROUND OF THE INVENTION

Orthodontic brackets are widely used to realign teeth through the application of corrective forces provided by interconnected archwires. To provide proper adjustment of the teeth, orthodontic brackets are typically attached to each tooth requiring treatment either with a band or directly thereto by a bonding material, and are then interconnected with a tensioned orthodontic archwire.

In edgewise brackets, the archwire passes through a labially opening, horizontal arch slot and is prebent and/or otherwise shaped to provide the desired corrective force to each individual tooth. The slot is directly accessible in order to allow, for example, an archwire to be readily placed therein. Once placed in the slot, an archwire is typically restricted therein by some device. Some of the more common retaining devices are: ligature wires, elastomeric ligatures, and metallic pins. The more frequently used devices are metallic ligature wires and elastomeric ligatures.

The archwire slot generally passes horizontally through one pair of tie wings in a single bracket or two pair of tie wings in a double bracket. In each pair of tie wings one wing tip extends gingivally and one wing tip extends occlusally. Thus when the archwire is placed within the slot, a ligature or elastomeric ligature may be placed around one tie wing, over the archwire in the slot and then around the other tie wing. If there are two pairs of tie wings, such as with a standard "SIAMESE"-type or double bracket, a single ligature or elastomeric ligature can be selectively positioned around either or both pair of tie wings to impart desired rotational forces to the tooth.

In the orthodontic treatment of teeth, it is important for the bracket (and interconnected tooth) to be capable of desired movement relative to the archwire in response to the corrective forces applied thereby. For example, in many situations, frictional engagement between the metal or elastomeric ligature and the archwire may negatively effect the treatment plan of the orthodontist. Alternatively, in certain treatment regimes it may also be desirable to allow for but limit restrictive engagement to selected distal or mesial pairs of tie wings of an edgewise bracket.

Double edgewise brackets offer more options for such selective ligation than is possible with standard single brackets due to their spaced apart pairs of tie wings. That is, in a double bracket, a single ligature may be placed around both pairs of tie wings together, or a separate ligature may be placed around each pair of tie wings (i.e., one separate ligature per pair), or one ligature may be placed around only one pair of tie wings. Whichever ligation option is selected, the use of known brackets results in direct contact with the archwire wherever the ligature crosses the archwire. Direct contact tends to force the archwire into the archwire slot and, therefore, increases frictional contact with the bracket during movement of the tooth along the archwire. As previously stated above, frictional contact between the archwire and the bracket in the archwire slot may undesirably slow down the prescribed treatment. For proper treatment, as previously stated above, the bracket must move along the archwire as desired. While it is important to retain the archwire in the bracket slot, any undesired friction therebetween prolongs the time it is necessary to conduct treatment. Thus, there is a need for an edgewise double bracket that allows greater ligation selectivity and reduces or eliminates undesired frictional interference between the ligature and the archwire and between the archwire and the bracket.

SUMMARY OF THE INVENTION

The invention disclosed herein comprises an edgewise orthodontic double bracket particularly useful for retaining an archwire in a slot while substantially reducing undesired frictional interference with treatment. More particularly, the invention allows for the reduction or elimination of undesired frictional archwire/double edgewise bracket slot interfaces as well as provides for increased ligation selectivity.

In one aspect of the present invention, an improved edgewise orthodontic double bracket of the type having a base and a plurality of pairs of protrusions extending therefrom for receiving an orthodontic archwire is provided. The bracket has at least one notch in oppositely facing sides of at least one pair of protrusions. A device for retaining the wire can be positioned within the notches to hold the wire within the bracket.

In another aspect of the present invention, two oppositely facing notches (e.g. gingivally and occlusally) are provided for each pair of protrusions. The device for retaining the wire may comprise a common metallic ligature wire or an elastomeric ligature.

In another aspect of the present invention the edgewise orthodontic bracket comprises a base, two pairs of tie wings attached to the base, and a slot through each pair of tie wings for receiving the orthodontic wire. At least one notch in each of the wing tips of each pair of tie wings receives a wire retaining device such that the wire retaining device can engage the wing tip to reduce or eliminate contact with the orthodontic wire and thus reduce frictional contact between the orthodontic wire and the bracket slot.

In one embodiment of the invention, a double bracket is provided with two pair of tie wings having oppositely facing wing tips. A labially opening mesiodistal archwire slot passes between the oppositely facing wing tips. An occlusal-gingival/vertical slot passes through a central support section proximate the midpoint between the pair of tie wings. An interbracket elastic hook is formed on the gingival tips of the tie wings. The sidewalls and the floor of the archwire slot are convexly shaped where the slot passes through each of the tie wings. The depth of the slot is slightly greater than a thickness of the archwire placed therein.

It is a technical advantage of the present invention that standard metallic ligature wires or elastomeric ligatures may be used with an edgewise orthodontic bracket with reduced frictional contact with the orthodontic wire, as may be desired, thus permitting greater control of any interference with treatment of the tooth by selective ligation. It is a further technical advantage that such contact may be controlled without adding to the mesiodistal length of the bracket, thereby maintaining interbracket distances. Any reduction of interbracket distances would undesirably increase the degree and angulation of torque which may be applied to each separate bracket and tooth.

It is a still further advantage of the present invention that frictional contact between the retaining device and the archwire may be controlled without adding to the labial-lingual height of the bracket. The addition of protrusions or extensions to the labial-lingual height of the bracket would tend to add to any discomfort the patient may already feel from the orthodontic appliances and is, therefore, undesirable.

BRIEF DESCRIPTION OF THE DRAWINGS

For a more complete understanding of the present invention and for further advantages thereof, reference is now made to the following Detailed Description taken in conjunction with the accompanying drawings, in which:

FIG. 6 is an alternative embodiment of the present invention;

FIG. 7 is an alternative use of the present invention;

FIG. 8 is a cross-sectional view of another alternative embodiment of the present invention;

FIG. 9 is an isometric view of the bracket of FIG. 2 illustrating one possible method of ligating;

DETAILED DESCRIPTION

Figure 1:
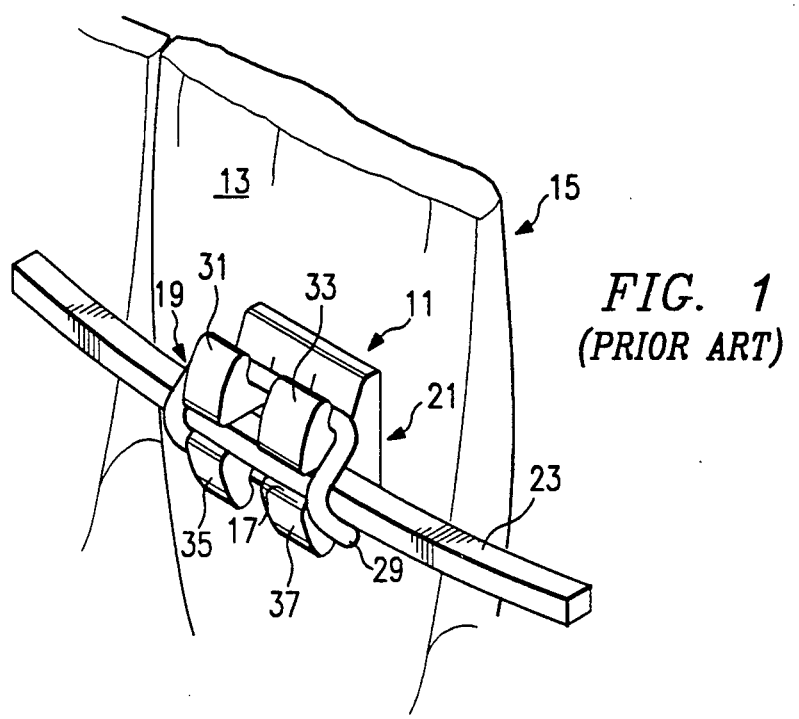
FIG. 1 is a bracket constructed in accordance with the prior art.

Referring to FIG. 1, a prior art bracket is generally identified by the reference numeral The bracket 11 is secured to a surface 13 of a tooth 15 by any method well known in the art such as by bonding thereto. The bracket 11 comprises, for example, a "SIAMESE" edgewise bracket having first and second pairs of tie wings 19 and 21. An orthodontic archwire 23 is inserted through a horizontal slot 17 opening labially therein. An archwire retaining device 29 such as, for example, a metallic ligature wire or an elastomeric ligature is installed on the bracket 11 for retention of the wire 23 within the slot 17. As shown, the wire 23 is rectangular but it is to be understood that the wire 23 could also be square or round depending upon the prescribed treatment. The slot 17 has a depth into the tie wings 19 and 21 less than or equal to the thickness (or diameter) of the archwire 23.

As is well known in the art, the device 29 is wrapped around wing tips 31, 33, 35 and 37 to retain the wire 23 in the slot 17. The device 29 typically contacts the wire 23 at the points where the device 29 crosses the slot 17 and is held in contact by the undersurface of the wing tips 31, 33, 35 and 37. Such contact creates friction therebetween as well as forcing the wire 23 into frictional contact with the floor of the slot 17. However, since it usually is desirable to allow the bracket 11 to slide along the wire 23 as the tooth 15 is adjusted thereby, interference with the desired treatment of the tooth 15 is possible.

Figure 2:
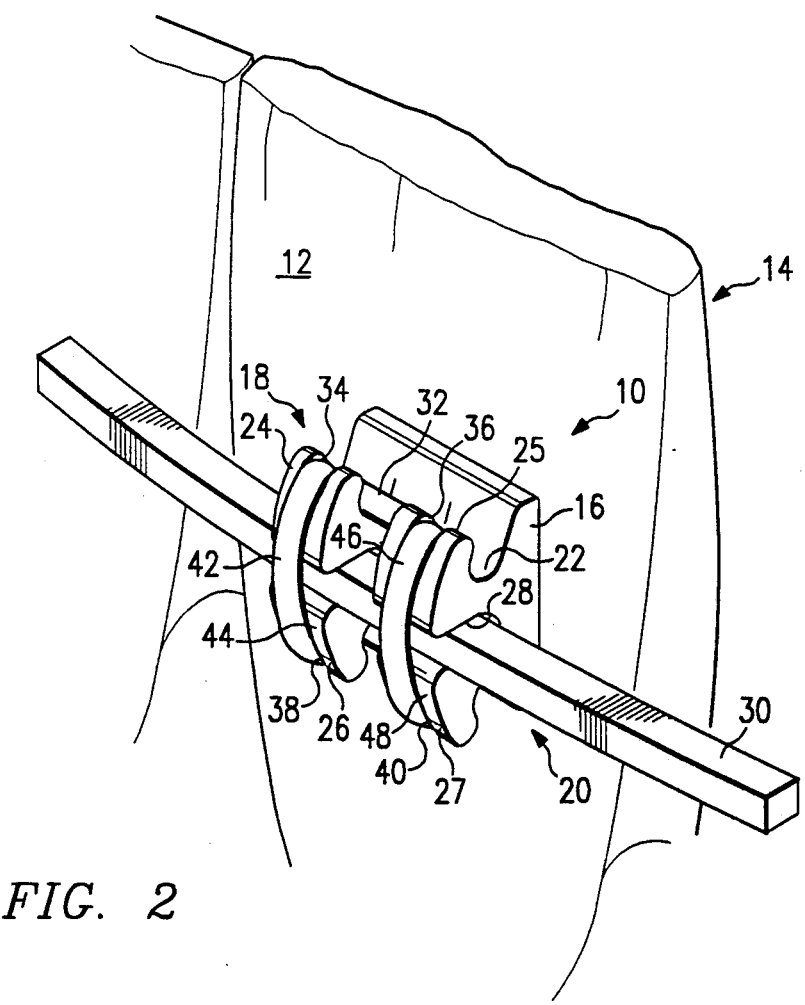
FIG. 2 is a perspective view of an orthodontic bracket constructed in accordance with an embodiment of the present invention.

Referring next to FIG. 2, a perspective view of an orthodontic bracket constructed in accordance with an embodiment of the present invention is generally identified by the reference numeral 10. The bracket 10 comprises an edgewise "SIAMESE" (or double) bracket. The bracket 10 is attached to a surface 12 of a tooth 14 by any known method such as by adhesive bonding. The surface 12 may be the lingual or labial surface of the tooth 14 depending upon the treatment technique utilized by the practitioner.

The bracket 10 is attached to the surface 12 by a base 16. First and second pairs of tie wings 18 and 20 are attached to the base 16, as is well known in the art, by a central support section 22. The first pair of tie wings 18 further comprises a pair of oppositely facing wing tips 24 and 26 while the second pair of tie wings 20 further comprises a pair of oppositely facing wing tips 25 and 27. A slot 28 passes between the wing tips 24 and 26, and between the wing tips 25 and 27. The slot 28 is provided for holding an orthodontic archwire 30, which may be rectangular, square or round, therein. The depth of the slot 28 into the tie wings 18 and 20 is greater than the thickness of the archwire 30, as will be subsequently described in greater detail.

Once the archwire 30 is inserted into the slot 28, it is necessary to provide a retaining device 32 to hold the wire 30 therein. It is a common practice in orthodontic treatment to use various retaining devices 32 such as, for example, an elastomeric ligature (shown) or a metallic ligature wire.

An elastomeric ligature comprises a one-piece loop which may be stretched around the wing tips and thus held in place thereon by its elastomeric characteristics (much like a rubber band). A metallic ligature wire comprises a length of a very fine and flexible wire which may be put into position around the bracket after which the ends thereof are twisted together.

In accordance with one embodiment of the present invention, the bracket 10 is provided with notches 34, 36, 38 and 40 in the wing tips 24, 25, 26 and 27, respectively. The notches 34, 36, 38 and 40 are generally concave in shape and extend into the wing tips 24–27. The notches 34, 36, 38 and 40 each have a mesiodistal width F (see FIG. 4) which is at least slightly greater (when using a metallic ligature wire) or slightly less (when using an elastomeric ligature) than a diameter of the retaining device 32 held therein. By making the width F no larger than necessary to hold the retaining device 32 therein, most of the structural strength of each wing tip 24, 25, 26 and 27 is retained, and the retaining force of the retaining device 32 on the wire 30, is kept as close to the mesial and distal edges of the bracket 10 as possible. In operation, the retaining device 32 is inserted into the notches 34, 36, 38 and 40 and across top surfaces 44 and 48 of the tie wings 18 and 20, as will be subsequently described in greater detail. The retaining device 32 is thus secured to the bracket 10 and serves to retain the wire 30 within the slot 28 without (or with reduced) undesired frictional contact between the wire 30 and the retaining device 32 thus also reducing undesired frictional contact and binding between the wire 30 and the slot 28.

Figure 3:
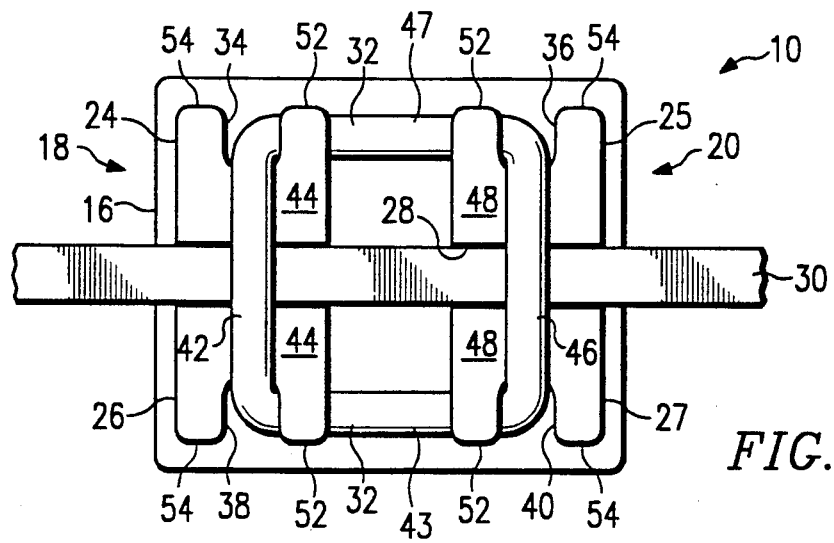
FIG. 3 is a top plan view of the bracket of FIG. 2.
Figure 4:
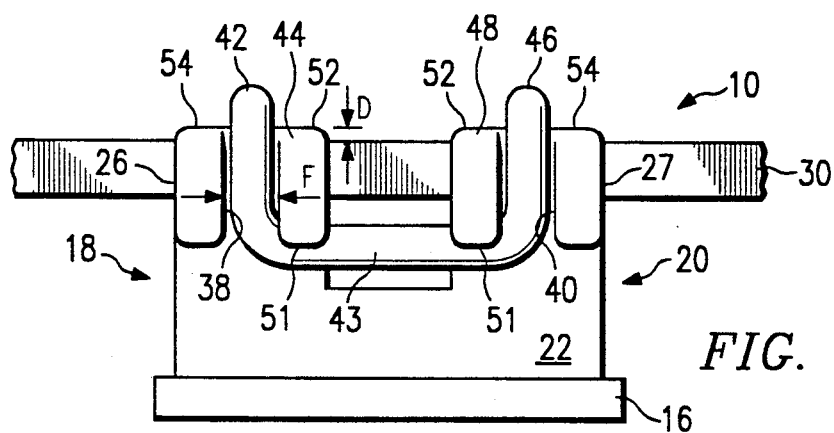
FIG. 4 is a gingival elevational view of the bracket of FIG. 2.

Referring simultaneously to FIGS. 3 and 4, the bracket 10 is further described in greater detail. In the top plan view of FIG. 3, the notches 34, 36, 38 and 40 can be seen to separate each of the wing tips 24, 25, 26 and 27 into first and second portions 52 and 54. The retaining device 32, for the sake of convenience of description, is divided into first portion 42, second portion 43, third portion 46, and fourth portion 47.

Thus, in operation, the retaining device 32 is positioned with the portions 42 and 46 over the top surfaces 44 and 48, respectively, of the first and second pairs of tie wings 18 and 20. The portion 43 is inserted into the notches 38 and 40 and under the portions 52 of the wing tips 26 and 27. The portion 47 of the device 32 is similarly placed into the notches 34 and 36 and under the portions 52 of the wing tips 24 and 25. Thus, the device 32 is secured to the bracket 10 and positioned over the slot 28 to retain (without touching) the wire 30 therein.

As best seen in FIG. 4, the device 32 passes under the portions 52 of the wing tips 26 and 27 and is retained therein by contact with undersurfaces 51 thereof. The notches 34, 36, 38 and 40 therefore serve as guides and holding members for the retaining device 32.

Also seen in FIG. 4, the portions 42 and 46 of the retaining device 32 are positioned a distance D above the wire 30 which is fully seated within the slot 28. Depending upon the particular dimensions of the slot 28, the wire 30, and the tie wings 18 and 20, the distance D will vary. Although not shown, it is to be understood that if so desired, the device 32 could provide desired frictional contact with the wire 30 (and thus frictional contact between the wire 30 and the slot 28) by wrapping around the wing tips 24, 25, 26 and 27, as is well known in the art and as described above in reference to FIG. 1.

Typical dimensions for orthodontic archwires include: round wire diameter of 0.016 inch, square wire sides of 0.0175-0.018 inch, and rectangular wires of 0.018 inch × 0.025 inch or 0.022 inch × 0.030 inch. Thus, the depth of the slot 28 must be at least slightly greater than the largest dimension of the wire to be placed therein. Although not shown, it is also to be understood that the floor of the slot 28 may be arcuate rather than planar. Thus, an archwire supporting floor surface, would be formed and the depth of the slot 28 would be determined from the highest point of the floor surface to the labial surface of the bracket.

Referring to FIG. 7, a positioning of the retaining device 32 on the bracket 10 for alternative selective ligation is shown. The portion 46 of the device 32 is passed under the undersurfaces 51 of both portion's 52 and 54 of the wing tip 27 (and the wing tip 25) in a conventional fashion. The portion 42, however, is inserted into the notch 38 (and the notch 34), as previously described above in reference to FIG. 3. Thus, the device 32 contacts the archwire 30 with the portion 46 and does not contact the archwire 30 with the portion 42 and selective frictional contact is available. By using the bracket 10 as described herein, it is possible to select various combinations of frictional contact or no contact between the device 32 and the wire 30 for various methods of treatment. Such selectivity is possible with the present invention without the necessity of extending the overall length or height of the brackets. Thus, no special techniques are needed to compensate for less space between adjacent brackets and no extra discomfort to the patient is created.

Referring to FIG. 9, another positioning of the retaining device 32 on the bracket 10 for a still further selective ligation alternative is shown. The portion 43 of the device 32 is passed under the undersurface 51 of the portion 52 of the wing tip 26 (and the portion 47 is similarly positioned with respect to the wing tip 24). The portion 46 is positioned between the tie wings 18 and 20 and connects the wing tips 26 and 24. In this manner of ligation, the portion 42 of the device 32 may be considered a leading end and the portion 46 may be considered a trailing end for the positioning thereof. Although not shown, it is to be understood that the portion 46 of the device 32 could be positioned over the archwire 30 along the mesial/distal edge of the wing 18. Both alternatives provide additional selective ligation options which can be of use during orthodontic treatment.

Figure 5:
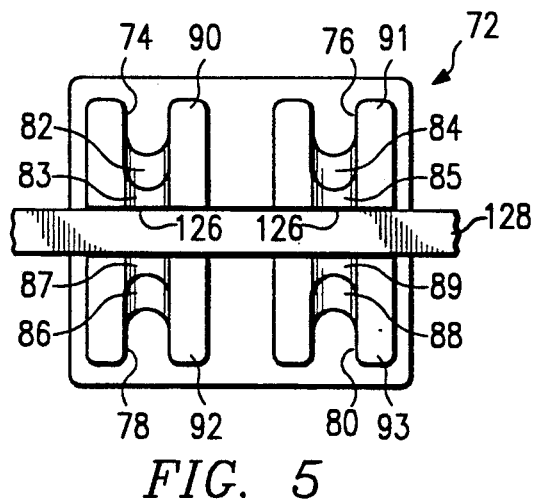
FIG. 5 is another embodiment of the present invention.

Referring to FIGS. 5 and 8, another embodiment of the present invention is generally indicated by the reference numeral 72. The bracket 72 is an edgewise double bracket constructed with four notches 74, 76, 78 and 80, as previously described above, but also including sloping surfaces 82, 84, 86 and 88 through wing tips 90, 91, 92 and 93, respectively. The sloping surfaces 82, 84, 86 and 88 terminate just prior to an archwire slot 126 leaving support landings 83, 85, 87 and 89, respectively.

When installing the retaining device in the bracket 72, the sloping surfaces 82, 84, 86 and 88 and the support landings 83, 85, 87 and 89 allow a retaining device 70 (see FIG. 8) to have a smaller distance to bridge over an archwire 128. Thus the retaining device is better able to resist escape of the archwire 128 from the slot 126 by a disruptive force and additionally facilitates placement of the retaining device by the practitioner. Wear on the retaining device is also reduced due to the reduction in the angle of bend therein needed to position the ligating device. As with the bracket 10 previously described above, the depth of the slot 126 is greater than the thickness of the archwire 128 to reduce undesired frictional contact with the retaining device.

Referring to FIG. 6, a bracket 94 is constructed in accordance with an alternative embodiment of the present invention. The bracket 94 has notches 96, 98, 100 and 102 formed in wing tips 104, 106, 108 and 110. The wing tips 104, 106, 108 and 110 are each split into portions 112 and 114 by the notches 96, 98, 100 and 102, respectively. In each case, the portions 114 are longer occlusal-gingivally than the portions 112. Such an arrangement may be helpful to further ensure that a retaining device is properly secured to the bracket 94 since the portions 114 provide greater undersurface area for contact therebetween. More importantly, the longer portions 114 are especially helpful for the practitioner during installation of the retaining device.

Figure 10:
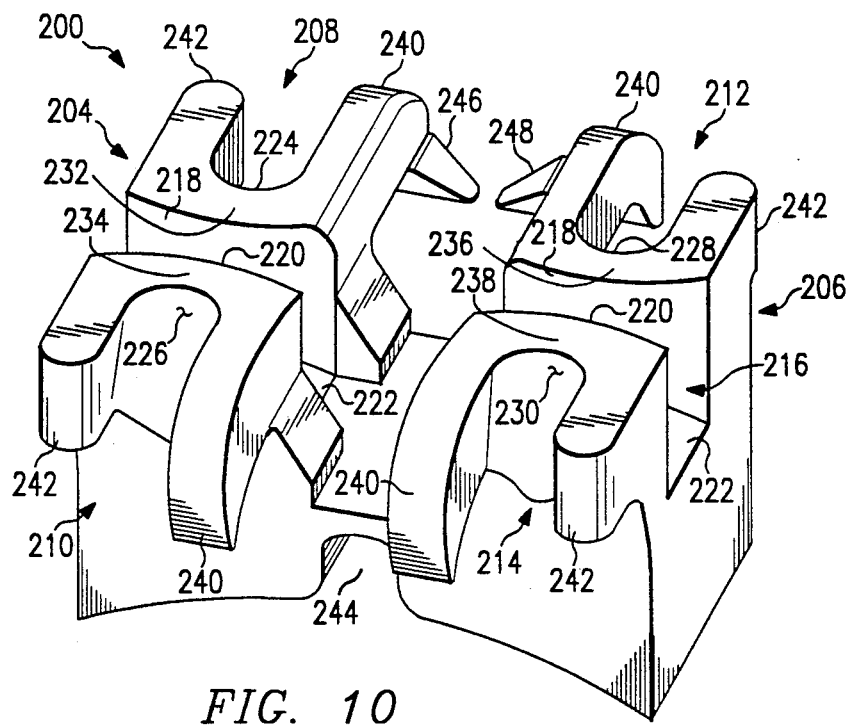
FIG. 10 is another alternative embodiment of the present invention.
Figure 11:
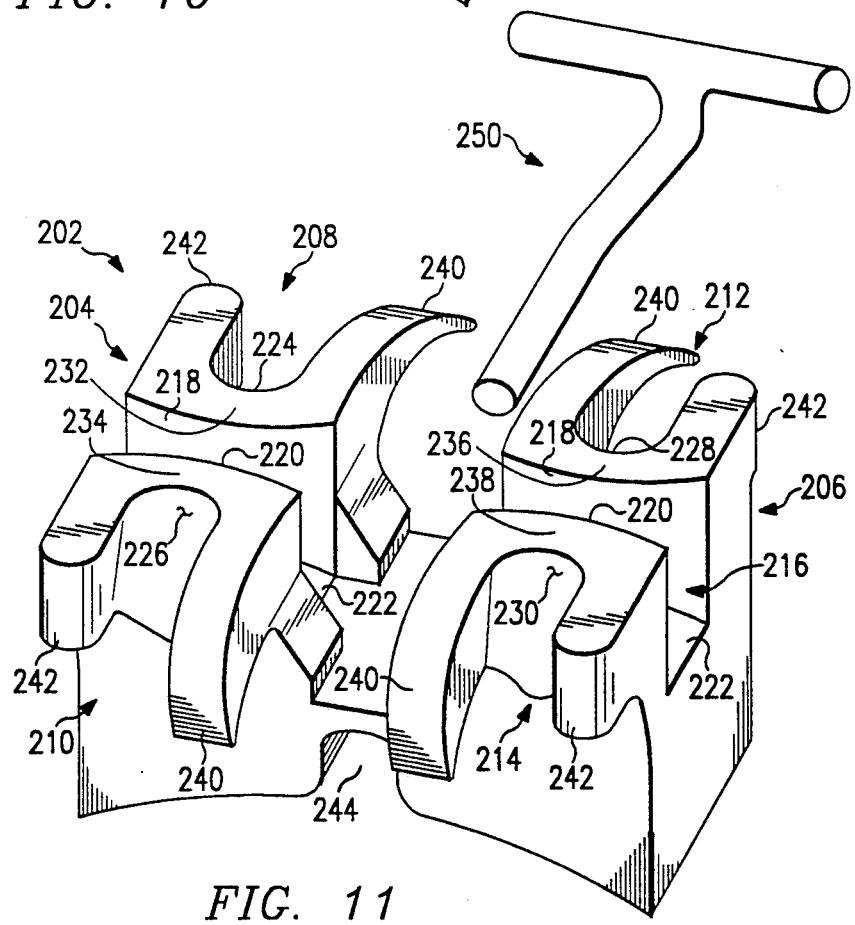
FIG. 11 is a further alternative embodiment of the present invention.

Referring to FIGS. 10 and 11, further alternative embodiments of the present invention are shown. Brackets 200 and 202 comprise double brackets each having two pair of tie wings 204 and 206, each pair having oppositely facing wing tips 208, 210, 212 and 214, respectively. A labially opening mesiodistal archwire slot 216 is formed through the tie wings 204 and 206. The slot 216 has convex sidewalls 218 and 220 and a transverse convex floor 222 where passing through the tie wings 204 and 206. The sidewalls 218 and 220 and the floor 222 are convex shaped to reduce frictional contact with an archwire received by the slot 216. The wing tips 208, 210, 212 and 214 each have a sloping surface sidewall notch 224, 226, 228 and 230, respectively, with support landings 232, 234, 236 and 238, as previously described above with reference to FIGS. 5 and 8. Also, as with the bracket 94 of FIG. 6, the wing tips 208, 210, 212 and 214 are each split into longer portions 240 and shorter portions 242 by their respective notches. An occlusal-gingival/vertical slot 244 passes through each bracket 200 and 202 proximate a midpoint thereof.

Referring to FIG. 10, a pair of hooks 246 and 248 are formed on the longer portions 240 of the wing tips 20 and 212. The hooks 246 and 248 allow inter-bracket elastic connections as desired. Alternatively, the bracket 202 of FIG. 11 can be modified by placing an accessory hook 250 into the vertical slot 244, as is known in the art. Although not shown, it is to be understood that any of the brackets as taught herein could be modified by the placement of conventional, integral, ball-type, interbracket elastic hooks.

The brackets constructed in accordance with the present invention are, therefore, capable of multiple arrangements in use with standard metallic wire ligatures and elastomeric ligatures. The archwire slot, in each case, is deeper than the cross-sectional thickness of the archwire to be used therewith. Thus, by selectively using one or more notch within the brackets, frictional contact between the retaining device and the archwire and thus the archwire and the bracket may be selectively decreased or increased as treatment requires.

Although the present invention has been described with respect to specific embodiments thereof, various changes and modifications may be suggested to one skilled in the art. Hence, it is intended that the present invention encompass such changes and modifications as fall within the scope of the appended claims.

I claim:

1. An improved edgewise orthodontic bracket of the type having a base for attachment to a tooth and at least one pair of tie wings extending therefrom, said at least one pair of tie wings defining a mesiodistal slot having a support floor surface for receiving an orthodontic archwire, wherein the improvement comprises:
   an occlusally facing notch and a gingivally facing notch on a periphery of said at least one pair of tie wings, wherein each of said notches of said at least one pair of tie wings is adapted for receiving a device for retaining the archwire in said slot, slopes upwardly from said periphery through at least a portion of one of said tie wings toward said slot, and has laterally displaced sidewall portions and a bottom portion which define a substantially arcuate surface, and wherein undesired frictional contact between the archwire and said device for retaining may be selectively reduced.

2. The bracket of claim 1, wherein said slot for receiving the archwire has a greater depth to said support floor surface than a height of the archwire when positioned in said slot.

3. The bracket of claim 1, wherein said notches of said at least one pair of tie wings further comprise:
   a generally concave shape.

4. The bracket of claim 1, wherein said device for retaining comprises:
   a metallic ligature wire.

5. The bracket of claim 4, wherein said notches of said at least one pair of tie wings further comprise:
   a mesiodistal width slightly greater than a thickness of said wire.

6. The bracket of claim 1, wherein said device for retaining comprises:
   an elastomeric ligature.

7. The bracket of claim 6, wherein said notches of said at least one pair of tie wings further comprise a mesiodistal width slightly less than a thickness of said elastomeric ligature.

8. The bracket of claim 1, further comprising:
   a support landing proximate said slot and an upper portion of each said notch of said at least one pair of tie wings.

9. The bracket of claim 1, wherein each said notch of said at least on pair of tie wings splits wing tips on said at least one pair of tie wings into a mesial tip and a distal tip, wherein at least one of said mesial or distal tips has an occlusal-gingival length greater than another of said mesial or distal tips.

10. The bracket of claim 1, further comprising:
    convex sidewalls where said slot passes through said at least one pair of tie wings, wherein at least a portion of said support floor surface is convex.

11. The bracket of claim 1, further comprising:
    an interbracket elastic hook formed integrally with said at least one pair of tie wings.

12. The bracket of claim 1, further comprising:
    a vertical accessary slot formed in the bracket.

13. An edgewise orthodontic bracket, comprising:
    at least one pair of tie wings attachable to a base;
    a mesiodistal slot between oppositely facing wing tips of said at least one pair of tie wings for receiving an orthodontic archwire, said slot having an archwire supporting floor surface; and
    a notch in an outer peripheral edge of each of said wing tips of said at least one pair of tie wings, each of said notches of said at least one pair of tie wings being adapted for receiving a device for retaining said archwire, having a surface sloping upwardly from a peripheral of said tie wing toward said slot through said wing tip, and having a support landing proximate said slot, wherein said device for retaining can be attached to said tie wings by said notches to retain said archwire in said slot.

14. The bracket of claim 13, wherein said slot further comprises:
    a greater depth to said archwire supporting floor surface than a height of said archwire when positioned in said slot.

15. The bracket of claim 13, wherein each said notch of said at least one pair of tie wings comprises:
    a concave shape.

16. The bracket of claim 13, wherein said device for retaining comprises:
    a metallic ligature wire.

17. The bracket of claim 16, wherein each said notch of said at least one pair of tie wings further comprises:
    a mesiodistal width slightly greater than a thickness of said wire.

18. The bracket of claim 13, wherein said device for retaining comprises:
    an elastomeric ligature.

19. The bracket of claim 18, wherein each said notch of said at least one pair of tie wings further comprises:
    a mesiodistal width slightly less than a thickness of said elastomeric ligature.

20. The bracket of claim 13, wherein said notches of said at least one pair of tie wings split each of said wing tips into a mesial tip and a distal tip, wherein one of said mesial or distal tips has a greater occlusal-gingival length than the other.

21. The bracket of claim 13, further comprising:
    convex sidewalls where said slot passes through said at least one pair of tie wings, wherein at least a portion of said supporting floor surface is convex.

22. The bracket of claim 13, further comprising:
an interbracket elastic hook formed integrally with the bracket.

23. The bracket of claim 13, further comprising:
a vertical accessary slot formed in the bracket.

24. An edgewise orthodontic bracket, comprising:
at least one pair of tie wings attachable to a base, each of said at least one pair of tie wings comprising an occlusally extending wing tip and a gingivally extending wing tip;
a slot between said wing tips of said at least one pair of tie wings for receiving an orthodontic archwire, said slot having an archwire supporting floor surface, said slot further comprising convex sidewalls where said slot passes through said wing tips, wherein at least a portion of said supporting floor surface is convex where said slot passes through said wing tips; and
an outwardly facing peripheral notch in each of said wing tips, each said notch of said at least one pair of tie wings being dimensioned to receive a device for retaining said archwire, wherein said device for retaining is attachable to the bracket by said notches to retain said archwire in said slot.

25. The edgewise orthodontic bracket of claim 24, wherein a depth of said slot to said supporting floor surface is greater than a height of said archwire when positioned in said slot.

26. The edgewise orthodontic bracket of claim 24, wherein said notches of said at least one pair of tie wings comprise:
a concave shape having a mesiodistal width;
a surface sloping upwardly from a peripheral edge of said wing tips toward said slot; and
a support landing proximate said slot.

27. The edgewise orthodontic bracket of claim 26, wherein said mesiodistal width is slightly greater than a thickness of said device for retaining.

28. The edgewise orthodontic bracket of claim 26, wherein said mesiodistal width is slightly less than a thickness of said device for retaining.

29. The bracket of claim 24, further comprising:
an interbracket elastic hook formed integrally with the bracket.

30. The bracket of claim 24, further comprising:
a vertical accessory slot formed in the bracket.

31. An improved edgewise orthodontic bracket of the type having a base for attachment to a tooth and at least one pair of protrusions extending therefrom defining a mesiodistal slot having a support floor surface for receiving an orthodontic archwire, wherein the improvement comprises:
an occlusally facing notch and a gingivally facing notch on a periphery of said at least one pair of protrusions for receiving a device for retaining the archwire in the slot, each of said notches of said at least one pair of protrusions further comprising a surface sloping upwardly from said periphery toward the slot and through said protrusion and a support landing proximate the slot;
wherein undesired frictional contact between the archwire and said device for retaining may be selectively reduced.

32. An edgewise orthodontic bracket, comprising:
at least one pair of tie wings attachable to a base, said at least one pair of tie wings comprising an occlusally extending wing tip and a gingivally extending wing tip;
a mesiodistal slot between said wing tips of said at least one pair of tie wings for receiving an orthodontic archwire, said slot having an archwire supporting floor surface; and
an outwardly facing peripheral notch in each of said wing tips of said at least one pair of tie wings, wherein said notches are dimensioned to receive a device for retaining said archwire, and wherein each of said notches comprise:
a concave shaped having a mesiodistal width;
a surface sloping upwardly from a peripheral edge of said wing tips toward said slot; and
a support landing proximate said slot;
wherein said device for retaining is attachable to the bracket by said notches to retain said archwire in said slot.

33. The edgewise orthodontic bracket of claim 32, wherein said mesiodistal width is slightly greater than a thickness of said device for retaining.

34. The edgewise orthodontic bracket of claim 32, wherein said mesiodistal width is slightly less than a thickness of said device for retaining.

35. An improved edgewise orthodontic bracket of the type having a base for attachment to a tooth and at least one pair of tie wings extending therefrom, said at least one pair of tie wings defining a mesiodistal slot having a support floor surface for receiving an orthodontic archwire, wherein the improvement comprises:
an occlusally-facing notch and a gingivally-facing notch on a periphery of said at least one pair of tie wings, wherein each of said notches of said at least one pair of tie wings is adapted for receiving a device for retaining the archwire in the slot, said device for retaining comprising an elastomeric ligature, wherein said notches of said at least one pair of tie wings each have a mesiodistal width which is slightly less than a thickness of said elastomeric ligature, and wherein undesired frictional contact between the archwire and said device for retaining may be selectively reduced.

36. An improved edgewise orthodontic of the type having a base for attachment to a tooth and at least one pair of tie wings extending therefrom, said at least one pair of tie wings defining a mesiodistal slot having a support floor surface for receiving an orthodontic archwire, wherein the improvement comprises:
an occlusally-facing notch and a gingivally-facing notch on a periphery of said at least one pair of tie wings, wherein each said notch of said at least one pair of tie wings splits wing tips on said at least one pair of tie wings into a mesial tip and a distal tip, one of said mesial or distal tips having an occlusal-gingival length greater than another of said mesial or distal tips, wherein each of said notches of said at least one pair of tie wings is adapted for receiving a device for retaining the archwire in the slot, and wherein undesired frictional contact between the archwire and said device for retaining may be selectively reduced.

* * * * *